US00PP25269P2

(12) United States Plant Patent
Oates

(10) Patent No.: US PP25,269 P2
(45) Date of Patent: Jan. 27, 2015

(54) ***ECHEVERIA* PLANT NAMED 'ECRPI01-0'**

(50) Latin Name: *Echeveria gibbiflora*
Varietal Denomination: ECRPI01-0

(71) Applicant: John David Oates, Tura Beach (AU)

(72) Inventor: John David Oates, Tura Beach (AU)

( * ) Notice: Subject to any disclaimer, the term of this patent is extended or adjusted under 35 U.S.C. 154(b) by 22 days.

(21) Appl. No.: 13/987,157

(22) Filed: Jul. 3, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Anne Grunberg
(74) *Attorney, Agent, or Firm* — Cassandra Bright

(57) ABSTRACT

A new and distinct *Echeveria* cultivar named 'ECRPI01-0' is disclosed, characterized by a tight rosulate plant form, unique leaf margins that are undulating, crenulate and bright pink. The new variety is an *Echeveria*, normally produced as an ornamental garden or container plant.

1 Drawing Sheet

Latin name of the genus and species: *Echeveria gibbiflora*.
Variety denomination: 'ECRPI01-0'.

BACKGROUND OF THE INVENTION

The new *Echeveria* cultivar is a product of a planned breeding program conducted by the inventor, John Oates, in Macquaires Fields, Australia. The objective of the breeding program was to produce new *Echeveria* varieties for ornamental commercial applications. The new variety is a product of crossbreeding that occurred on Apr. 11, 2005, at a commercial nursery in Macquaires Fields, Australia.

The seed parent is the unpatented, proprietary seedling variety of *Echeveria gibbiflora*, 'Line 541'. The pollen parent is the unpatented, proprietary seedling variety *Echeveria gibbiflora*, 'Line 190'. The new variety was discovered during January of 2006 by the inventor in a group of seedlings resulting from the 2005 crossing, in a commercial nursery in Macquaires Fields, Australia.

Asexual reproduction of the new cultivar has been performed by tissue culture. This was first performed at a laboratory in Tumbi Umbi, Australia in March of 2008 and has shown that the unique features of this cultivar are stable and reproduced true to type in 15 successive generations.

SUMMARY OF THE INVENTION

The cultivar 'ECRPI01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECRPI01-0'. These characteristics in combination distinguish 'ECRPI01-0' as a new and distinct *Echeveria* cultivar:

1. Very strong and consistent undulation of leaf margin.
2. Undulating foliage.
3. Unique leaf blade coloration of grey-green with a strong, bright pink margin color.
4. Rosulate plant form.

PARENT COMPARISON

Plants of the new cultivar 'ECRPI01-0' are similar to plants of the seed parent, unpatented, proprietary seedling variety of *Echeveria gibbiflora* 'Line 541' in most horticultural characteristics, however, plants of the new cultivar 'ECRPI01-0' produce a leaf margin with stronger undulation, and a thicker bright pink margin coloration.

Plants of the new cultivar 'ECRPI01-0' are similar to plants of the pollen parent; *Echeveria gibbiflora* 'Line 190' in most horticultural characteristics, however, plants of the new cultivar 'ECRPI01-0' produces leaves that are greyed-green, with a strong bright pink margin, whereas the pollen parent produces green foliage with a thin pink margin. The new variety has foliage which does not fade in high temperatatures.

COMMERCIAL COMPARISON

'ECRPI01-0' can be compared to the commercial variety *Echeveria gibbiflora* 'ECRAQ03-0', filed concurrently, having application Ser. No. 13/987,155. Plants of 'ECRPI01-0' are similar to plants of 'ECRAQ03-0' in most horticultural characteristics, however, plants of 'ECRPI01-0' produce leaves with bright pink margin, whereas 'ECRAQ03-0' produces a red margin. The margin coloration of plants of 'ECRPI01-0' is thicker and more consistent than the margin of plants of 'ECRAQ03-0'. Additionally, plants of 'ECRPI01-0' produce leaves that do not change color with temperatures changes 'ECRPI01-0' can be compared to the commercial variety *Echeveria gibbiflora* 'ECRRE02-0', filed concurrently, having application Ser. No. 13/987,156. Plants of 'ECRPI01-0' are similar to plants of 'ECRRE02-0' in most horticultural characteristics, however, plants of 'ECRPI01-0' produce leaves with an undulating margin, compared to the crenulated margin of 'ECRRE02-0'. Additionally, 'ECRRE02-0' fades somewhat under high temperatures, whereas 'ECRPI01-0' does not fade under high temperatures

BRIEF DESCRIPTION OF THE PHOTOGRAPH

The accompanying photograph in FIG. 1 illustrates in full color a typical plant of 'ECRPI01-0'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ECRAQ03-0' plants grown in a greenhouse in Oxnard, Calif. The growing temperature ranged from approximately 15° C. to 28° C. during the day and from 12° C. to 22° C. during the night. General light conditions are bright, normal sunlight. Measurements and numerical values represent averages of typical plant types. Measurements were taken from plants grown in warm temperatures, during Spring and Summer.
Botanical classification: *Echeveria gibbiflora* 'ECRPI01-0'.

PROPAGATION

Propagation method: Tissue culture.

PLANT

Age of plant described: Approximately 14 months from tissue culture.
Container size: 1 gallon nursery container.
Height: Approximately 14 cm to top of highest leaf.
Plant spread: Approximately 29 cm.
Growth rate: Slow.
Branching characteristics: To date, only a single rosette, without branches observed.

FOLIAGE

Leaf:
*Arrangement*.—Rosette.
*Average length*.—Approximately 10 cm.
*Average width*.—Approximately 14 cm.
*Shape of blade*.—Broad deltate.
*Aspect*.—Undulating.
*Apex*.—Rounded crenulate.
*Base*.—Obuse.
*Margin*.—Undulating and somewhat crenulate.
*Texture of top surface*.—Glabrous.
*Texture of bottom surface*.—Glabrous.
*Quantity of leaves per plant*.—Approximately 15 large leaves, and 5 smaller immature inner leaves.
*Color*.—Young foliage upper side: Near RHS Greyed-Green 191C, margin near RHS Red 46C. Young foliage under side: Near RHS Greyed-Green 191C, margin near RHS Red 46C. Mature foliage upper side: Near RHS Greyed-Green 191A, margin near RHS Red 46C. Mature foliage under side: Near RHS Near RHS Greyed-Green 191A, margin near Red 46C.
*Venation*.—Type: Linear. Venation color upper side: Indistinguishable from foliage. Venation color under side: Indistinguishable from foliage.

FLOWER

Flowering not observed to date.

REPRODUCTIVE ORGANS

None observed to date.

OTHER CHARACTERISTICS

Seeds and fruits: No seeds-fruits detected to date.
Disease/pest resistance: Neither resistance nor susceptibility to the normal diseases and pests of *Echeveria* have been observed.
Temperature tolerance: Tolerates temperatures from approximately 0° C. to at least 40° C.

What is claimed is:

1. A new and distinct cultivar of *Echeveria* plant named 'ECRPI01-0' as herein illustrated and described.

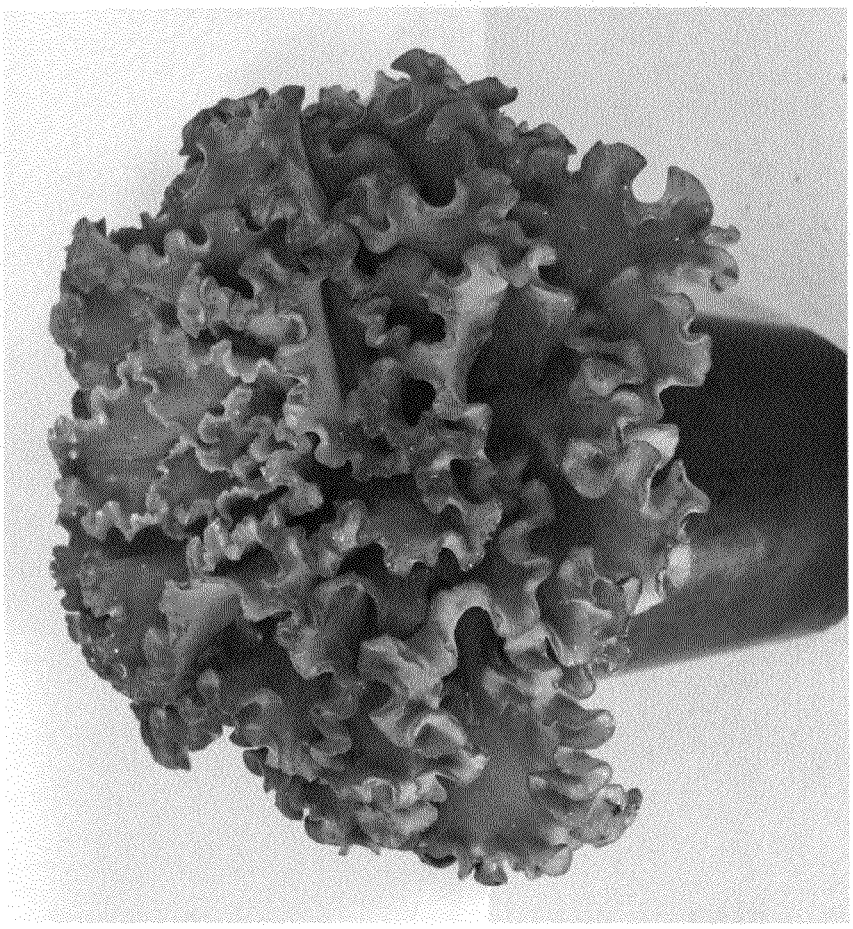

* * * * *